United States Patent [19]

Lee

[11] Patent Number: 5,037,811
[45] Date of Patent: Aug. 6, 1991

[54] 4-(OXYGEN, SULFUR OR NITROGEN SUBSTITUTED)-METHYL 5-HYDROXY-2(5H)-FURANONES AS ANTI-INFLAMMATORY AGENTS

[75] Inventor: Gary C. M. Lee, Laguna Hills, Calif.

[73] Assignee: Allergan, Inc., Irvine, Calif.

[21] Appl. No.: 510,368

[22] Filed: Apr. 17, 1990

[51] Int. Cl.$^5$ .................. A61K 31/665; A61K 31/47; C07D 305/12; C07D 9/06
[52] U.S. Cl. ..................................... 514/99; 514/313; 514/318; 549/214; 549/222; 549/213; 549/318
[58] Field of Search ............... 549/222, 313, 318, 214; 514/99, 471, 473

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,455 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |

FOREIGN PATENT DOCUMENTS

| | | |
|---|---|---|
| 133376 | 2/1985 | European Pat. Off. |
| 209274 | 1/1987 | European Pat. Off. |
| 295056 | 6/1987 | European Pat. Off. |

OTHER PUBLICATIONS

Bonjouklian et al., Chemical Abstracts, vol. 106, 156260c, p. 670 (1987).
Reynolds et al, J. Am. Chem. Soc., 110, pp. 5172–5177 (1988).
Tocanne et al., Chemical Abstracts 69, 76581k, p. 7146 (1968).
Deems et al, Biochimica et Biophysica Acta, 917, pp. 258–268 (1987).
Scheuer et al., Journal of the American Chemical Society, 100:1, p. 307 (Jan. 4, 1978).
Graziano et al., Chemical Abstracts 107 (1987), 236559t.
Negishi et al., J. Org. Chem 45, pp. 5223–5225 (1980).

Primary Examiner—Cecilia Shen
Attorney, Agent, or Firm—Gabor L. Szekeres; Robert J. Baran; Martin A. Voet

[57] ABSTRACT

Compounds of the formula

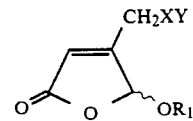

in which $R_1$ is H or alkyl of 1 to 20 carbons, $CO-R_1^*$ $CO-O-R_1^*$ $CO-NH-R_1^*$ or $PO(OR_1^*)_2$ or $PO(OR_1^*)R_1^*$ where $R_1^*$ independently is H, alkyl of 1 to 20 carbons, phenyl, or substituted phenyl; X is O, S, SO—, $SO_2$, NH—, or $NR_2$ where $R_2$ is phenyl, substituted phenyl or alkyl of 1 to 20 carbons, and Y is alkyl having at least 6 carbon atoms, arylalkyl, aryl, substituted aryl, substituted arylalkyl, alkenyl containing one or more olephinic bonds and at least 6 carbon atoms, $CO-R_3$, $CO-OR_3$, $CONHR_3$, $SO_2R_3$, $SO_2NHR_3$ where $R_3$ is aryl, substituted aryl, substituted arylalkyl, alkyl, alkenyl containing one or more olephinic bonds, further Y is $(CH_2)_n-O-R_4$, or $(CH_2)_n-O-(CH_2)_m-O-R_4$, where n, and m, are integers and are independently 1 to 25 and $R_4$ is phenyl, substituted phenyl or alkyl of one to 20 carbons, still further Y is $PO(OH)_2$, $PO(OH)OR_5$, $PO(OH)R_5$ $PO(OR_5)_2$, where $R_5$ is independently phenyl, substituted phenyl, alkyl or 1 to 20 carbons or $R_5$ is $(CH_2)_n-N(R_5^*)_3$ where $R_5^*$ is alkyl of 1 to 20 carbons, or Y is $NH-R_6$ where $R_6$ is phenyl, substituted phenyl or alkyl of at least 6 carbon atoms with the proviso that when X is O, S, then Y is not $NH-R_6$, and with the further proviso that when X is SO or $SO_2$ then Y is not $SO_2R_3$ or $SO_2NHR_3$, are disclosed. The compounds possess anti-inflammatory activity.

63 Claims, No Drawings

4-(OXYGEN, SULFUR OR NITROGEN SUBSTITUTED)-METHYL 5-HYDROXY-2(5H)-FURANONES AS ANTI-INFLAMMATORY AGENTS

BACKGROUND OF THE INVENTION

1. Field of the Invention

The present invention is directed to novel 4-(oxygen, sulfur or nitrogen substituted)-methyl 5-hydroxy-2(5H)-furanones which compounds are active as anti-inflammatory agents. The present invention is also directed to pharmaceutical compositions which comprise one or more of the novel compounds of the invention, to the methods of using these pharmaceutical compositions, and to the chemical processes of making the novel compounds.

2. Brief Description of the Prior Art

Manoalide is a compound isolated from a marine sponge [E. D de Silva et al., *Tetrahedron Letters* 21:1611–1614 (1980)] which has anti-inflammatory, immunosuppressive and analgesic properties. Manoalide (Compound 1) the structure of which is shown below, includes a 5-hydroxy-2(5H)-furanone moiety, attached in the 4-position of the furanone ring to the rest of the molecule. Certain analogs of manolide, such as seco-manoalide (Compound 2) and dehydro-seco-manoalide (Compound 3) also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

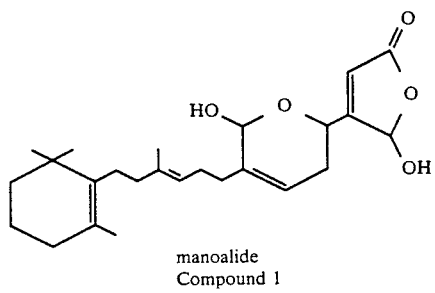

manoalide
Compound 1

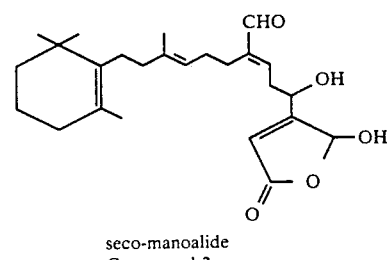

seco-manoalide
Compound 2

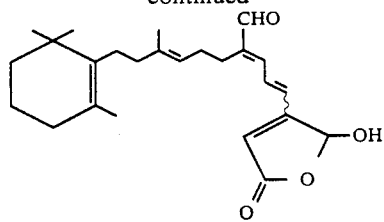

dehydro-seco-manoalide
Compound 3

Synthetic analogs of manoalide, particularly analogs having various substituents on the furanone moiety of manoalide, are described in several applications for U.S. Letters Patent by the same inventor as in the present application, the following of which have been allowed and are expected to issue as U.S. Letters Patent:

Ser. No. 259,225 filed on Oct. 18, 1988;
Ser. No. 281,126 filed on Dec. 7, 1988.

Published European Patent Application No. 0 295 056 discloses 4-substituted 5-hydroxy-2(5H)-furanones having anti-inflammatory, immunosuppressive and anti-proliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

SUMMARY OF THE INVENTION

The present invention covers compounds of Formula 1,

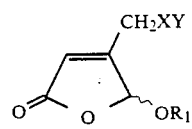

Formula 1 in which $R_1$ is H or alkyl of 1 to 20 Carbons, $CO-R_1^*$ $CO-O-R_1^*$ $CO-NH-R_1^*$ or $PO(OR_1^*)_2$ or $PO(OR_1^*)R_1^*$ where $R_1^*$ independently is H, alkyl of 1 to 20 carbons, phenyl, or substituted phenyl; X is O, S, $SO-$, $SO_2$, $NH-$, or $NR_2$ where $R_2$ is phenyl, substituted phenyl or alkyl of 1 to 20 carbons, and Y is alkyl having at least 6 carbon atoms, arylalkyl, aryl, substituted aryl, substituted arylalkyl, alkenyl containing one or more olephinic bonds and at least 6 carbon atoms, $CO-R_3$, $CO-OR_3$, $CONHR_3$, $SO_2R_3$, $SO_2NHR_3$ where $R_3$ is aryl, substituted aryl, substituted arylalkyl, alkyl, alkenyl containing one or more olephinic bonds, further Y is $(CH_2)_n-O-R_4$, or $(CH_2)_n-O-(CH_2)_m-O-R_4$, where n, and m, are integers and are independently 1 to 25 and $R_4$ is phenyl, substituted phenyl or alkyl of one to 20 carbons, still further Y is $PO(OH)_2$, $PO(OH)OR_5$, $PO(OH)R_5$ $PO(OR_5)_2$, where $R_5$ is independently phenyl, substituted phenyl, alkyl of 1 to 20 carbons or $R_5$ is $(CH_2)_n-N(R_t^*)_3$ where $R_5^*$ is alkyl of 1 to 20 carbons, or Y is $NH-R_6$ where $R_6$ is phenyl, substituted phenyl or alkyl of at least 6 carbon atoms with the proviso that when X is O, S, then Y is not NH-R$_6$, and with the further proviso that when X is SO or SO$_2$ then Y is not SO$_2$R$_3$ or SO$_2$NHR$_3$.

The present invention also covers salts of the above-defined compounds, formed with pharmaceutically acceptable acids or bases, as applicable.

In a second aspect the present invention relates to pharmaceutical formulations comprising one or more compounds of Formula 1 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

In still another aspect, the present invention relates to the processes of making the compounds of Formula 1. In general terms, these processes, shown in a summarized fashion in Reaction Scheme 1 comprise the steps of reducing a 2-trialkylsilyl-4-furaldehyde (Formula 2) with a reducing agent, such as sodium borohydride, to provide a 2-trialkylsilyl-4-hydroxymethylfuran of Formula 3. Alternatively, a 2-trialkylsilyl-4-furaldehyde (Formula 2) is reacted with hydroxylamin, or with a hydroxylamin derivative, such as NH$_2$OCH$_3$, and the resulting oxime is reduced to provide a 2-trialkylsilyl-4-aminomethylfuran (Formula 4). When desired, sulfur is introduced into the molecule (when in general Formula 1 X=S) for example by replacing the hydroxyl function of the compounds of Formula 3 with a suitable leaving group (such as iodine) and thereafter subjecting the resulting intermediate (e. g., 2-trialkylsily-4-iodomethylfuran) to a nucleophilic substitution reaction with a reagent of the formula Y'—SH. The resulting sulfur containing 2-trialkylsilylfuran derivative of Formula 5 is reacted with singlet oxygen to provide compounds of Formula 1 where X is sulfur and R$_1$ is hydrogen.

To obtain compounds of Formula 1 where X is oxygen, the intermediate 2-trialkylsilyl-4-hydroxymethylfuran of Formula 3 is reacted with a reagent of the formula Y'—L and the intermediate Formula 6 is thereafter treated with singlet oxygen. Compounds of Formula 1 where X is NH or NR$_2$, (R$_2$ defined as in Formula 1) are obtained by reacting the 2-trialkylsilyl-4-aminomethylfuran of Formula 4 with the reagent of the formula Y'—L, and thereafter treating the intermediate of Formula 7 with singlet oxygen. In these reactions and particularly in the reagents Y'—SH and Y'—L, Y' symbolizes either the Y group (as Y is defined in connection with Formula 1) or such a precursor of the Y group which may be readily converted into Y through reactions within the skill of the practicing organic chemist. L usually symbolizes a leaving group, or such a group which is adapted for the reaction that couples the Y' function to the hydroxyl or amino function in the respective hydroxymethyl or aminomethyl side chain in the 4-position of the 2-trialkylsilylfuran molecule. L may be a halogen, so that Y'—L may be an alkyl halide or an acylhalide. L may also be OH, for example when the reagant Y'—L is condensed with the compound of Formula 3 in the presence of dicyclohexylcarbodiimide (DCC) and 4-dimethylaminopyridine (DMAP) to form an ester. The reagent Y'— L may also symbolize an isocyanate, in which case L symbolizes N=C=O and Y' symbolizes the R$_3$ group as R$_3$ is defined in connection with Formula 1.

Reaction Scheme 1

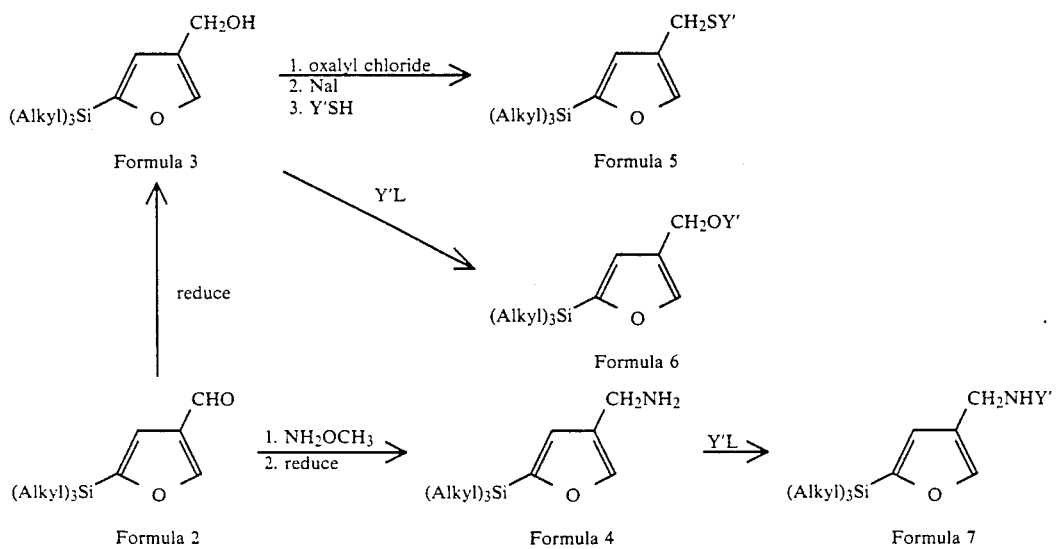

-continued
Reaction Scheme 1

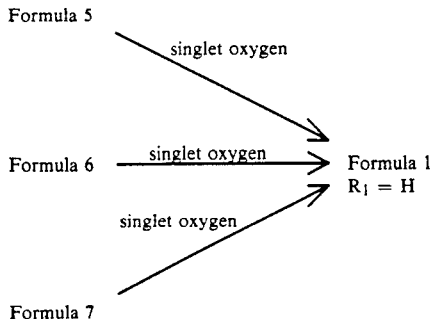

When it is desired to substitute (acylate, alkylate or the like) the 5-hydroxy function of the compounds of Formula 1, an $R_1$ group (as defined in connection with these formulas) can be introduced into the 5-hydroxy-2(5H)-furanone compounds by conventional means.

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, the term "long chain alkyl" also means the former broad definition of "alkyl" groups but with the restriction that the group has no less than 4 carbon atoms, and no more than approximately 25 carbon atoms.

Unless specifically noted otherwise, preferred amides are the mono- and di-substituted amides derived from the saturated aliphatic radicals of ten or fewer carbon atoms, or the cyclic or saturated aliphatic-cyclic radicals of 5 to 10 carbon atoms.

Some of the compounds of the invention may contain a chiral center. Other compounds of the invention may contain more than one chiral center. Accordingly, the compounds of the invention may be prepared as mixtures of enantiomeric compounds (where the enantiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the abovenoted forms, including optically pure enantiomers and mixtures thereof, as well as all diastereomers, are within scope of the present invention.

Some of the compounds of the invention may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such a mono-, di- or tri-acid may also be used.

The preferred compounds of the present invention are, with reference to Formula 1 and with respect to the 5-position of the furanone moiety, those where the substituent is hydroxy, acetoxy or alkanoyloxy derived from an alkanoic acid including a long chain alkyl group ($R_1$ is H, $CH_3CO$, or is $CO-R_1^*$ where $R_1^*$ is long chain alkyl). Particularly preferred in this regard are the compounds where $CO-R_1^*$ is n-dodecanoyl.

With respect to the X substituent in the side chain in the 4-position of the 5-hydroxy-2(5H)-furanone molecule, the preferred compounds of the invention are those where X is O, S, NH, SO, and $SO_2$.

With respect to the Y substituent in the side chain in the 4-position of the 5-hydroxy-2(5H)-furanone molecule, the preferred compounds of the invention are those where Y is long chain alkyl, particularly where the alkyl group is straight chained and has more than 10 carbons; the n-dodecyl group is especially preferred in this regard. Compounds are also preferred where Y is $(CH_2)_n-O-(CH_2)_m-O-R_4$, particularly where n is 1, m is 2, and $R_4$ is methyl. Further with respect to the substituent group Y, compounds are preferred where Y is CO—$R_3$, CO—$OR_3$, $CONHR_3$, $SO_2R_3$, $SO_2NHR_3$ and where $R_3$ is long chain alkyl, particularly straight chained long chain alkyl, most preferably where $R_3$ is n-dodecyl. Alternatively, compounds are preferred in the latter category where $R_3$ is phenyl substituted straight chain alkyl of at least 4 carbons (or substituted phenyl substituted straight chain alkyl of at least 4 carbons); in certain particularly preferred embodiments of the invention Y is CO—$R_3$ with $R_3$ being 5-(4-methoxyphenyl)-n-pentyl. Still, further, compounds are preferred within the scope of the present invention where Y is $PO(OH)_2$, $PO(OH)R_5$, where $R_5$ is long chain alkyl, preferably long chain n-alkyl, most preferably n-dodecyl, or Y is $PO(OR_5)_2$, where $R_5$ is lower alkyl, most preferable ethyl, and still further where Y is $PO(OH)O(CH_2)_n-N^+(R_t*)_3$ particularly when n is 2 and where $R_5*$ is methyl.

The most preferred compounds of the invention are those listed below with reference to Formula 1.

entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties

| Compound 4: | X = O | $R_1$ = H | Y = $CH_2O(CH_2)_2OCH_3$; |
|---|---|---|---|
| Compound 5: | X = O | $R_1$ = H | Y = $PO(OH)(CH_2)_{11}CH_3$; |
| Compound 6: | X = O | $R_1$ = H | Y = $CONH(CH_2)_{11}CH_3$; |
| Compound 7: | X = O | $R_1$ = H | Y = $(CH_2)_{11}CH_3$; |
| Compound 8: | X = NH | $R_1$ = H | Y = $CO(CH_2)_{11}CH_3$; |
| Compound 9: | X = NH | $R_1$ = H | Y = $CONH(CH_2)_{11}CH_3$; |
| Compound 10: | X = NH | $R_1$ = H | Y = $SO_2(CH_2)_{11}CH_3$; |
| Compound 11: | X = S | $R_1$ = H | Y = $(CH_2)_{11}CH_3$; |
| Compound 12: | X = SO | $R_1$ = H | Y = $(CH_2)_{11}CH_3$; |
| Compound 13: | X = O | $R_1$ = H | Y = $PO(OCH_2CH_3)_2$; |
| Compound 14: | X = O | $R_1$ = $CO(CH_2)_{10}CH_3$ | Y = $PO(OCH_2CH_3)_2$; |
| Compound 15: | X = O | $R_1$ = H | Y = $POO^-O(CH_2)_2N^+(CH_3)_3$; |
| Compound 16: | X = NH | $R_1$ = H | Y = $COO(CH_2)_{11}CH_3$; |
| Compound 17: | X = NH | $R_1$ = H | Y = $PO(OH)(CH_2)_{11}CH_3$; |
| Compound 18: | X = $SO_2$ | $R_1$ = H | Y = $(CH_2)_{11}CH_3$; |
| Compound 19: | X = O | $R_1$ = H | Y = $CO(CH_2)_5$—(4-methoxy)phenyl; |
| Compound 20: | X = NH | $R_1$ = H | Y = $SO_2NH(CH_2)_{11}CH_3$; |
| Compound 21: | X = O | $R_1$ = $CO(CH_2)_{10}CH_3$ | Y = $PO(OH)_2$. |

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells, etc. Calcium is inhibited from In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration Pharmaceutical compositions of this invention comprise compounds of Formula I and of Formula 2, and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such composition may be used. Preferably, compositions for topical administration will contain 0.05-5% of the active ingredient.

A typical cream formulation may contain the following:

| Ingredient | Parts by Weight |
|---|---|
| Water/glycol mixture (15% or more glycol) | 50-99 |

-continued

| Ingredient | Parts by Weight |
| --- | --- |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (mobilization) Inhibition Assay

Polymorphonuclear leukocytes (PMNa), gastric glands, GH$_3$ cells, A431 cells, spleen cells, human keratinocytes corneal cells, etc. were loaded with the Ca$^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431cells were detached using a 5-10 min trypsin-EDTA treatment whereas GH3 cells were treated 2 to 5 min with a 1% pancreatin solution. Cells were immediately washed twice in a 20mM HEPES buffer (pH 7.4) containing 120mM NaCl, 6 mM KCl, 1 mM MgSO$_4$, 1 mg/ml glucose and 1 mg/ml pyruvate and 1.4mM calcium (medium A). Approximately $5 \times 10^6$ cells were suspended in medium A and incubated with 4uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340nm and emission wavelength set at 500nm. The cell suspension was continually stirred, maintained at 37° C. and equilibrated for approximately 5 min before addition of various agents. [Ca$^{2+}$i was calculated using the following formula:

$$[Ca^{2+}]_i = 220 \times \frac{F - F_{min}}{F_{max} - F}$$

All fluorescence values were measured relative to a EGTAquenched signal determined as follows: F was the relative fluorescence measurement of the sample. $F_{max}$ was determined by lysing the cells with digitonin (100ug/ml) in DMSO. After $F_{max}$ was determined the pH was adjusted to 8, with NaOH and Ca$^{2+}$ chelated with 3mM EGTA to totally quench the fura-2 signal and obtain $F_{min}$.

When quin-2- was used, cells were incubated with 10uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900-904].

Inhibition of Phosoholioase A$_2$

The effect of compounds of this invention on bee venom phospholipase A$_2$ is determined by the following procedure:

a. Bee venom phospholipase A$_2$ in 10 uM HEPES (pH 7.4) with 1 mM CaCl$_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.

c. Start the reaction by the addition of enzyme (0.495 units/ml).

d. Incubation for 15 sec. at 41°.

e. Reaction is terminated by addition of 2.5 ml of isopropanol: n-heptane: 0.5 M H$_2$SO$_4$ (40:10:1; v:v:v:).

f. 2.0 ml n-heptane and 1.0 ml H$_2$O added; mixture centrifuged.

g. 2.0 ml n-heptane removed and treated with 200-300 mg of silica gel HR60.

h. Samples centrifuged; 1 ml of n-heptane SN removed and added to 10 ml scintillation fluid.

i. Samples counted on a scintillation counter.

Inhibition of Phosphoinositide-specific Phospholipase C

The effect of compounds of this invention on phosphoinositide-specific phospholipase C may be determined by procedures described by Bennett et al, *Molecular Pharmacology* 32:587–593 (1987).

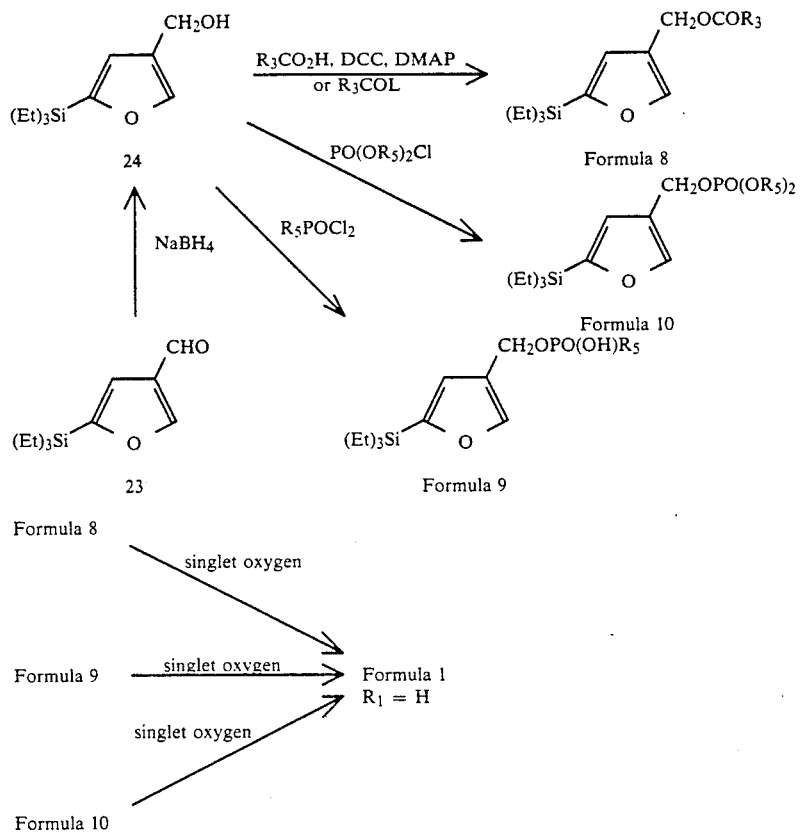

Reaction Scheme 2

ACTIVITY DATA

In the above-described phospholipase $A_2$ assay the compounds of the invention were found to provide 50% inhibition ($IC_{50}$) of bee venom phospholipase $A_2$ at the following concentrations (in micromoles), as indicated in Table 1.

TABLE 1

| Phospholipase $A_2$ Assay. | |
| --- | --- |
| Compound name or number | $IC_{50}$ (um) |
| 1* | 0.03 |
| 4 | >1 |
| 5 | 0.03 |
| 6 | 0.05 |
| 7 | 0.04 |
| 8 | 0.26 |
| 9 | 0.13 |
| 10 | 0.04 |
| 11 | 0.06 |
| 13 | 0.34 |

*Data for Compound 1 (monoalide) are provided for comparison.

SPECIFIC EMBODIMENTS

The compounds of the present invention can be made by the synthetic chemical pathways which are illustrated here in general terms, and in the specific examples as well. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention.

Referring now to Reaction Scheme 2, a general process is shown for preparing compounds of the invention which are derivatives of 5-hydroxy-4-hydroxymethyl-2(5H)furanone (in Formula 1 X is oxygen). The reaction sequence starts with a 2-trialkylsilyl4-furaldehyde, such as 2-trimethylsilyl-4-furaldehyde (Compound 22) or preferably with 2-triethylsilyl-4-furaldehyde (Compound 23) These starting compounds can be made in accordance with several procedures known in the chemical literature. The preferred method for the synthesis of compound z3 , however, is described in the application for U.S. Pat. Ser. No. 259,225, filed on Oct. 18, 1988, now allowed, and assigned to the same assignee as the present application. The processes for the syntheses of these important starting materials (Compounds 22 and Compound 23) are also described here in detail in the ensuing section of Specific Examples.

Thus, utilizing the specific example of 2-triethylsilyl-4-furaldehyde (Compound 23), this starting material is reacted with a suitable reducing agent, preferably with sodium borohydride, in a suitable solvent, such as methanol, to provide (2-triethylsilyl-4-furyl)methanol (Compound 24). In the event Compound 22 is used as the starting material, then 2-trimethylsilyl-4-furyl)methanol (Compound 25) is obtained in the reduction. In order to obtain compounds of the invention which are esters (in Formula 1 X=O and Y=$COR_3$, $R_3$ defined as in connection with Formula 1), 2-triethylsilyl-4-furyl)methanol (Compound 24) or Compound 25 are reacted with an acyl halide of the formula $R_3CO$—L (L is halogen) preferably in the presence of an acid acceptor such as triethylamine, or in a mildly basic solvent such as pyridine. A preferred method for preparing compounds of the invention which are esters, however, is to condense 2-triethylsilyl-4-furyl)methanol (Compound 24) or Compound 25 with a carboxylic acid of the formula R₃COOH) in the presence of dicyclohexylcarbodiimide (DCC) and 4-dimethylaminopyridine (DMAP).

The resulting 4-acyloxymethyl-2-triethylsilylfuran of Formula 8 is thereafter reacted with singlet oxygen to provide esters of Formula 1 where the 5-hydroxyl group of the furan moiety is unsubstituted ($R_1 = H$). In the event it is desired to introduce an $R_1$ group (as defined in connection With Formula 1) such as an alkyl or acyl group, into the Compounds of Formula 1, this can be accomplished by reactions within the skill of the practicing organic chemist.

Referring back to the reaction of the 4-acyloxymethyl-2-triethylsilylfuran intermediates of Formula 8 with singlet oxygen, as well as to the reaction of other intermediates (described later in this specification) with singlet oxygen, the conditions of these reactions are described in detail in connection with several specific examples. In general terms, the reactions are preferably conducted in a mixture of water and acetone or in a mixture of water and tetrahydrofuran, and in some instances in substantially neat tetrahydrofuran, in the presence of an initiator, preferably Rose Bengal dye (preferably polymer bounded), which is added to the reaction mixture. The reaction mixture and vessel is flushed with oxygen and the reaction is conducted at low temperature, at approximately $-78°$ C., or for the herein described reactions preferably at approximately $0°$ C., under a constant positive pressure of oxygen for a number of hours, typically 1 to 7 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

Generally speaking most transformations (except introduction of a substituent $R_1$ on the 5-hydroxyl group) leading to the compounds of the present invention are preferably performed before reacting the 2-trialkylsilylfuran derivative with singlet oxygen. Nevertheless, the foregoing preference is not always applicable, and as those having ordinary skill in the art will readily recognize, the compounds obtained in the "singlet oxygen oxidation step" may themselves be subjected to certain reactions (such as oxidation on sulfur when $X = S$) to obtain further compounds of the invention.

Referring back again to Reaction Scheme 2, in order to obtain phosphonyl esters of 4-hydroxymethyl-5-hydroxy-2(5H)furanone, the intermediates 2-triethylsilyl-4-furyl)methanol (Compound 24) or Compound 25 are reacted with a corresponding phosphonyldichloride which has the formula $R_5POCl_2$ ($R_5$ defined as in connection with Formula 1) to give, after hydrolysis of the second chloro group, the intermediate of Formula 9.

In order to obtain phosphate esters of 4-hydroxymethyl-5-hydroxy-2(5H)-furanone the intermediates 2-triethylsilyl-4-furyl)methanol (Compound 24) or Compound 25 are reacted with a corresponding phosphorylchloride ($PO(OR_5)_2Cl$, $R_5$ defined as in Formula 1) to give the intermediate phosphate esters of Formula 10. Treatment of the intermediate compounds of Formula 9 and of Formula 10 with singlet oxygen, respectively, provides the phosphonate and phosphate esters of Formula 1 where $R_1$ is hydrogen. The phosphate esters of Formula 10, such as diethyl (2-triethylsilyl-4-furyl-methyl phosphate (in Formula 10 $R_5 =$ ethyl) can be selectively deesterified to provide (2-triethylsilyl-4-furyl)methylphosphate (in Formula 10 $R_5 = H$) by treatment with trimethylsilyl bromide. The resulting phosphoric acid mono-ester intermediate provides, after treatment with singlet oxygen, the phosphoric acid ester of 4-hydroxymethyl-5-hydroxy-2(5H)-furanone (Formula 1, $X = O$ and $Y = PO(OH)_2$).

Reaction of the intermediates (2-triethylsilyl-4-furyl)-methanol (Compound 24) or Compound 25 with a sulfonyl chloride reagent of the formula $R_3SO_2Cl$ ($R_3$ defined as in Formula 1) followed by treatment with singlet oxygen provides sulphonate esters of the invention (in Formula 1 $X = O$ and $Y = SO_2R_3$).

Referring now to Reaction Scheme 3, a general process is illustrated to obtain compounds of the invention which comprise ethers formed from 4-hydroxymethyl-5-hydroxy-2(5H)-furanone, for example, compounds where, With reference to Formula 1, $X = O$ and Y is alkyl or arylalkyl. Thus, the intermediates 2-triethylsilyl-4-furyl)methanol](Compound 24) or Compound 25 are reacted with an appropriate alkyl halide in the presence of base to provide the intermediate ethers of Formula 11. In Reaction Scheme 3 Y'—L symbolizes for example, an alkyl halide, an aralkyl halide, or the like, which is capable of forming an ether linkage with Compound 24. Examples of halides (reagents of the formula Y'—L) which are used in this reaction are 2-methoxyethoxymethyl chloride and dodecyliodide. The relatively reactive 2-methoxyethoxymethyl chloride reacts with Compound 24 in the presence of a weak base, such as dimethylaniline, while reaction of dodecyliodide with Compound 24 is conducted in the presence of strong base, such as potassium hydride. The intermediate ether of Formula 11 yields, after reaction with singlet oxygen, compounds of Formula 1 where $R_1$ is hydrogen.

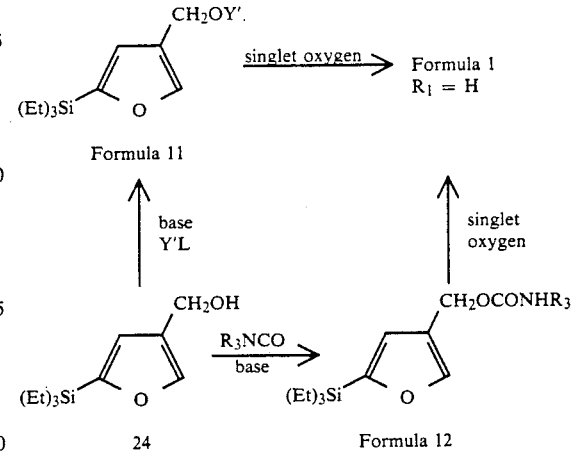

Reaction Scheme 3

Reaction Scheme 3 also demonstrates a generalized process for preparing compounds of the present invention which are 4-carbamoyloxymethyl-5-hydroxy-2(5H)-furanone derivatives, that is where, with reference to Formula 1, X is 0 and Y is $CONHR_3$ ($R_3$ defined as in connection with Formula 1). In accordance with this process, Compound 24 or Compound 25 are reacted with an isocyanate of the formula R₃-NCO, preferably in the presence of a strong base. An example of an isocyanate used for making Compound 6 of the present invention is dodecylisocyanate; the reaction is conducted in tetrahydrofuran (THF) in the presence of potassium bis(trimethylsilyl)amide as a base. Referring again to the Formula 14 are treated with singlet oxygen to yield compounds of Formula 1, where R₁ is hydrogen and X is S or SO2, respectively. As is further shown in Reaction Scheme 4, the thioethers of Formula 1 can be oxidized with a suitable oxidizing agent, such as hydrogen peroxide to yield the sulfoxides of Formula 1.

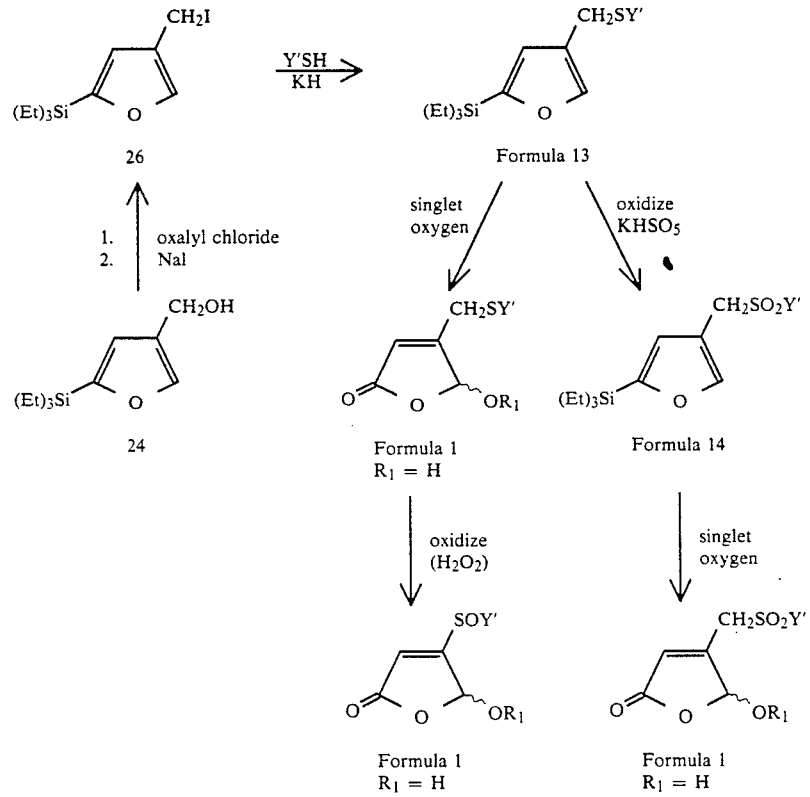

general scheme of Reaction Scheme 3, the intermediate carbamate derivative of Formula 12 is reacted with singlet oxygen to provide the compounds of Formula 1 where R₁ is hydrogen.

Reaction Scheme 4 illustrates reactions leading to compounds of the invention which are thioeters, sulfoxides and sulfonates, that is where, with reference to Formula 1, X is S, SO or SO₂. In accordance with this scheme, 2-triethylsilyl-4-furyl)methanol (Compound 24) or Compound 25 are converted into the corresponding iodo derivative, 4-iodomethyl-2-triethylsilylfuran (Compound 26). This is accomplished preferably by reacting Compound 24 with oxalyl chloride and thereafter by treating the resulting intermeoxalyldiate bis [(2-triethylsilyl-4-furyl)methyl]oxalate (Compound 27) with sodium iodide. 4-iodomethyl-2-triethylsilylfuran (Compound 26) is thereafter treated with a thiol of the formula Y'—SH in the presence of strong base, such as potassium hydride, preferably in the presence of hexamethylphosphoramide. In the thiol reagent Y' symbolizes either the Y group (as defined in connection with Formula 1) preferably an alkyl or aralkyl group, or such a precursor of the Y group which can be readily converted into the Y group by chemical reactions within the skill of the practicing organic chemist. The resulting intermediate thioether of Formula 13 is converted to the corresponding sulfon of Formula 14 by oxidation with a suitable reagent, such as potassium peroxymonosulfate. The thioether of Formula 13 and the sulfon of Reaction Scheme 5 describes, in general terms, synthetic processes leading to compounds of the invention which are derivatives of 4-aminomethyl-5-hydroxy-2(5H)-furanone, that is compounds where, with reference to Formula 1, X=NH2 Thus, in accordance with this reaction sequence, 2-trimethylsilyl-4-furaldehyde (Compound 22) or preferably 2-triethylsilyl-4-furaldehyde (Compound 23) is reacted with methoxylamine hydrochloride to form O-methyl-2-triethylsilyl-4-furaldehyde oxime (Compound 2s). 0-methyl-2-triethylsilyl-4-furaldehyde oxime (Compound 2s) is reduced, preferably with sodium borohydride, to yield 4-aminomethyl-2-triethylsilyl-furan (Compound 29). Compound 29 may be acylated with a reagent having the formula R₃CO—L, which is preferably an acyl halide (R₃ is defined as in connection with Formula 1, L is preferably Cl), to yield intermediate amides of Formula 15. The latter acylation reaction with an acyl halide, such as dodecanoyl chloride, is preferably conducted in the presence of an acid acceptor, such as triethylamine, in a neutral solvent, such as tetrahydrofuran. Oxidation with singlet oxygen of the compounds of Formula 15 yields the compounds of the invention which are amides, and where R₁ is hydrogen.

In order to prepare urea derivatives of the invention, that is compounds where, with reference to Formula 1, X is NH and Y is CONHR₃, the intermediate 4- aminomethyl-2-triethylsilyl-furan (Compound 29) is reacted with an isocyanate of formula R₃NCO, where R₃ is defined as in connection with Formula 1. As a specific example, the reaction of dodecyl isocyanate with Compound 29 in tetrahydrofuran, in the presence of triethylamine is noted to yield after singlet oxygen oxidation, the herein described specific Compound 9. The intermediate 2-triethylsilyl-4-furylmethylurea derivatives of Formula 16 yield, after oxidation with singlet oxygen, compounds of Formula 1 where $R_1$ is hydrogen.

hol of the formula $R_3OH$ ($R_3$ defined as in connection with Formula 1). Thus Compound 29 is reacted with $R_3OCOCCl_3$ (where $R_3$ is for example dodecyl) to provide the intermediates of Formula 18. The compounds of Formula 18 are oxidized with singlet Oxygen to yield the carbamate compounds of the invention where the 5-hydroxy group of the furan moiety is unsubstituted.

Continuing still with the description of Reaction Scheme 5, reaction of 4-aminomethyl-2-triethylsilyl-furan (Compound 29) with a phosphonyldichloride having the formula $R_5POCl_2$ ($R_5$ defined as in connec-

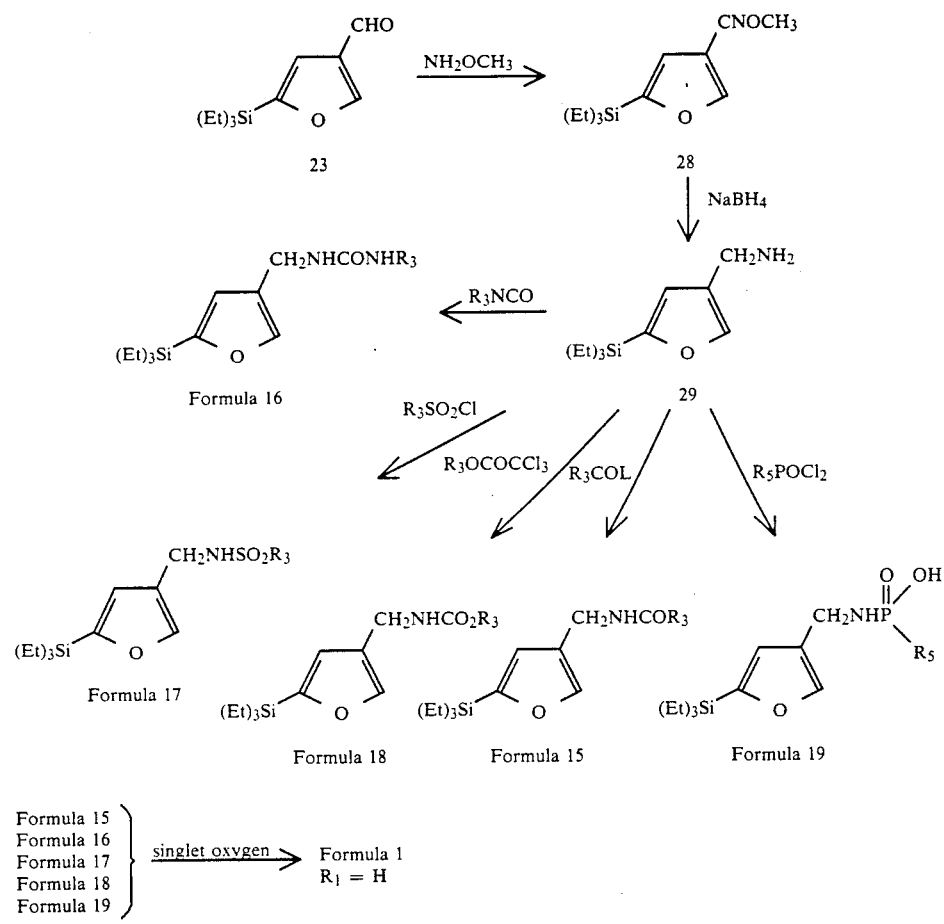

As is shown further in Reaction Scheme 5, 4-aminomethyl-2-triethylsilyl-furan (Compound 29) is reacted with a sulfonyl halide (preferably sulfonyl chloride) of the formula $R_3SO_2Cl$ to provide the sulfonamide intermediates of Formula 17. This reaction too, like the analogous acylation with an acyl halide, is advantageously conducted in the presence of triethylamine in a neutral solvent, such as tetrahydrofuran. n-Dodecylsulfonyl chloride serves as an example for the reagent $R_3SO_2Cl$. The intermediate sulfonamides of Formula 17 are oxidized with singlet oxygen to provide sulfonamide compounds of the invention, where $R_1$ is hydrogen.

To prepare compounds of the invention which are carbamates derived from 4-aminomethyl-5-hydroxy-2(5H)-furanone (i.e. in Formula 1 X=NH and Y=COOR₃) the intermediate 4-aminomethyl-2-triethylsilyl-furan (Compound 29) is preferably reacted with a diphosgene (Cl₃CCOCCl₃) "activated" ester of an alcotion with Formula 1) provides the intermediate phosphonamides of Formula 19. The compounds of Formula 19 are converted by oxidation with singlet oxygen to the 5-hydroxy2(5H)furanone derivatives of the invention. In order to obtain compounds of the invention which are alkyl- or aralkylaminosulfonylamides (in other words: sulfonylureas; in Formula 1 X is NH, and Y is SO₂NHR₃, R₃ defined as in connection with Formula 1) first sulfonyldichloride is reacted with an amine of the formula R₃NH₂, the resulting alkylaminosulfonylchloride (R₃NHSO₂Cl) is reacted with 4-aminomethyl-2-triethylsilyl-furan (compound 29), and the latter reaction is followed by oxidation with singlet oxygen.

The following examples of specific compounds of the invention, and specific examples of the synthetic steps in which the compounds and certain intermediates are made, are set out to illustrate the invention, not to limit its scope.

EXAMPLE 1

2-Trimethylsilyl-4-furaldehyde (Compound 22)

n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. 48°–50°/0.25 torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) −2.0, 116.2, 128.9, 155.3, 164.1 and 184.5.

HRMS exact mass calculated for $C_8H_{12}O_2Si(M^+)$ 168.0607, found 168.0588.

4-Hydroxymethyl-2-trimethylsilylfuran (Compound 25)

2-Trimethylsilyl-4-furaldehyde (Compound 22) (1.57 g, 9.35 mmol) was added to a suspension of sodium borohydride (424 mg, 11.2 mmol) in methanol (10 ml) at 0° C. After 45 minutes, most of the methanol was evaporated and the residue taken up in ethyl ether. The ethyl ether extracts were combined, washed (water), dried (magnesium sulfate) and evaporated to dryness to give an oil, which was purified by flash chromatography on silica using 30% ethyl ether/hexane to give the title alcohol as a pale yellow oil.

$^1$H NMR (CDCl3): 7.57 (s, 1H); 6.64 (s, 1H); 4.50 (s, 2H); 2.75 (broad s, 1H); 0.25 (s, 9H).

$^{13}$C NMR (CDCl3) 161.5, 144.0, 125.0, 119.7, 56.2, −1.8.

HRMS exact mass calculated for $C_8H_{14}O_2Si$: 170.0763, obtained (EI+): 170.0766.

4-(Methoxyethoxymethoxymethyl)-2-trimethylsilylfuran (Compound 30)

2-Methoxyethoxymethyl chloride (0.11 ml, 0.96 mmol) was added to a solution of 4-hydroxymethyl-2-trimethylsilylfuran (Compound 25, also known as (2-trimethylsilyl-4-furyl)methanol, 162.8 mg, 0.96 mmol) and dimethylaniline (0 13 ml, 0.1 mmol) in dichloromethane (5 ml) at 0°. After stirring at room temperature overnight (ca. 16 hours), the reaction mixture was washed successively with water, dilute hydrochloric acid and water. Evaporation of the dried (magnesium sulfate) dichloromethane layer gave an oil, which was purified by preparative silica TLC (developed with 30% ethyl ether/hexane) to give the title ether as a colorless oil.

$^1$H NMR (CDCl3) 0.27 (s, 9H), 3.44 (s, 3H), 3.62 (m, 2H), 3.76 (m, 2H), 4.51 (s, 2H), 4.79 (s, 2H), 6.67 (s, 1H), and 7.65 (s, 1H). MS m/e (% abundance 258(M+, 23), 182(19), 169(57), 154(72), 153(80), 89(50), 73)100) and 59(33).

4-Methoxyethoxymethoxymethyl)-5-hydroxy-2(5H)-furanone (Compound 4)

A mixture of 4-(methoxyethoxymethoxymethyl)-2-trimethylsilylfuran (Compound 30, 106 mg, 0.41 mmol) and Rose Bengal (ca. 3.0 mg) in tetrahydrofuran (7 ml) was exposed to singlet oxygen at −78° for 2 hours. The residue, after solvent removal, was purified by chromatography on preparative silica thin layer plates (developed with 40% ethyl acetate/hexane) to give the title furanone as a colorless oil.

$^1$HNMR (CDCl$_3$) 3.43 (s, 3H), 3.61, 3.75 (2 br s, 4H), 4.51 (s, 2H), 4.84 (s, 2H) and 5.30 (br, 1H), 6.11 (s, 1H) and 6.14 (s, 1H)

$^{13}$C NMR (CDCl$_3$) 58.9, 62.7, 67.1, 71.6, 95.9, 97.8, 118.7, 165.3 and 170.6.

EXAMPLE 2

2-Triethylsilyl-4-furaldehyde (Compound 23)

n-Butyl lithium (a 2.5M solution in hexane; 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 2 hours before triethylsilylchloride 13.4 ml, 80.1 mmol) was added. Stirring was continued overnight (14 hours) while the cooling bath was allowed to attain room temperature. The solution was poured into ice cold 10% (v/v) hydrochloric acid (100 ml) and after stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethylsily-3-furaldehyde as a pale yellow oil, boiling point 85°–90°/0.4 torr.

IR (neat) 1680cm$^{-1}$ $^1$H NMR (CDCl$_3$) 0.79 (q, 6H, J =7.3 Hz), 0.90 (t, 9H, J =7.3 Hz), 7.0 (s, 1H), 8.26 (s, 1H) and 9.95 (s, 1H).

$^{13}$C NMR (CDCL$_3$) 2.9, 7.1, 117.2, 128.8, 155.6, 162.3 and 184.6.

HRMS m/e exct mass calculated for $C_{11}H_{18}O_2Si(M^+)$ 210.1076, found 210.1071.

4-Hydroxymethyl-2-triethylsilylfuran (Compound 24)

Sodium borohydride (353 mg, 0.93 mmol) was added portionwise to a solution of 2-triethylsilyl-4-furaldehyde (compound 23, 1.64 g, 7.79 mmol) in methanol (10 ml) at 0°. After 1 hour, most of the methanol was evaporated and the residue dissolved in a minimum amount of dilute hydrochloric acid. Extraction (ethyl acetate), drying (magnesium sulfate) and evaporation gave an oil, which was purified by flash chromatography on silica using 20% ethyl ether/hexane. Fractions with $R_f$ of about 0.07 (10% ethyl ether/hexane) gave after evaporation the title alcohol as a colorless oil.

$^1$HNMR (CDCl$_3$) 0.76 (q, 6H, J =7.4 Hz), 0.97 (t, 9H, J =7.5 Hz), 1.45 (t, 1H, J =5.3 Hz), 4.56 (d, 2H, J =5.3 Hz), 6.67 (s, 1H) and 7.62 (s, 1H).

HRMS exact mass calculated for $C_{11}H_{20}SiO_2(M^+)$ 212.1233 found 212.1231.

4-(dodecylphosphonyloxymethyl)-2-triethylsilylfuran (Compound 3)

Dodecylphosphinic dichloride (944 mg, 3.29 mmol) was added to a solution of 4-hydroxymethyl-2-triethylsilylfuran (Compound 24, also known as (2-triethylsilyl-4-furyl)methanol 696.8 mg, 3.29 mmol) and 4-dimethylaminopyridine (403 mg, 3.29 mmol) in tetrahydrofuran (5 ml) at 0°. After stirring at room temperature overnight (15 hours), a solution of potassium hydroxide (235 mg, 3.62 mmol) in water (ca. 3 ml) was added. After 30 minutes, the solution was diluted with water and extracted thoroughly with ethyl acetate. Evaporation of the dried (magnesium sulfate) extracts gave an oil, which was purified by flash chromatography on silica using 40% ethyl ether/hexane to give the title ester as a pale yellow oil. $^1$HNMR (CDCl$_3$) 0.75 (q, 6H, J =8.1 Hz), 0.90 (t, 3H, J =6.9 Hz), 0.99 (t, 9H, J =7.8 Hz), 1.27 (br s, 18H), 1.55 (m, 2H), 1.90 (m, 2H), 4.90 (m, 2H), 6.70 (s, 1H) and 7.68 (s, 1H).

MS m/e (% abundance) 444(M+, 12), 388(100), 335(22), 195(21) and 115(21).

4-(Dodecylohosohonyloxymethyl)-5-hydroxy-2(5H)-furanone (Compound 5)

A mixture of 3-(dodecylphosphonyloxymethyl)-5-triethylsilylfuran (Compound 31, 325 mg, 0.73 mmol), Rose Bengal (ca. 5 mg) and water (ca. 0.05 ml) in tetrahydrofuran (10 ml) was exposed to singlet oxygen at 0° C. for 1.5 hours. The residue, after solvent removal, was purified by chromatography on preparative silica thin layer plates (developed with 5% methanol/dichloromethane) to give the title furanone.

$^1$HNMR (CDCl$_3$) 0.91 (t, 3H, J =6.2 Hz), 1.29 (br s, 16H), 1.40 (m, 2H), 1.65 (br m, 1H), 1.95 (m, 1H), 4.95 (br, 2H), 6.15 (br s, 1H), 6.18 (br s, 1H) and 7.0 (br, 1H).

$^{13}$CNMR (CDC13) 13.9, 21.9, 22.5, 23.9, 25.7, 28.7, 28.9, 29.2, 29.3, 29.5, 30.2, 30.5, 31.7, 60.8, 97.5, 118.6, 163.3, 163.4 and 170.4.

FABMS (negative ion) 361[(M-H)+, 9]and 249(72).

EXAMPLE 3

4-(N-Dodecylcarbamoyloxymethyl)-2-triethylsilylfuran (Compound 32)

Potassium bis(trimethylsilyl)amide (a 0.5M solution in toluene; 0.7 ml, 0.36 mmol) was added to a solution of 4-hydroxymethyl-2-triethylsilylfuran Compound 24, 76.1 mg, 0.36 mmol) in tetrahydrofuran (2 ml) at 0° under argon. After 30 minutes, a solution of dodecylisocynate (151 mg, 0.72 mmol) in tetrahydrofuran (0.5 ml) was added. Stirring was continued overnight (14 hours) while the cooling bath attained room temperature. The reaction mixture was quenched with water and extracted thoroughly with ether. Evaporation of the dried (magnesium sulfate) extracts gave an oil, which was purified by preparative silica TLC (developed with 10% ethyl ether/hexane) to give the title carbonate as a pale yellow oil.

$^1$HNMR (CDCl$_3$) 0.77 (q, 6H, J =8.0 Hz), 0.91 (t, 3H, J =6.9 Hz), 1.00 (t, (H, J=7.3 Hz), 1.29 (br s, 18H), 1.50 (m, 2H), 3.20 (m, 2H), 4.72 (br, 1H), 5.00 (br s, 2H), 6.69 (s, 1H) and 7 69 (s, 1H).

HRMS exact mass calculated for C$_{24}$H$_{45}$SiNO$_3$(M+) 423.3168, found 423.3164.

4-(N-Dodecylcarbamoyloxymethyl)-5-hydroxy-2(5H)-furanone (Compound 6)

A mixture of 3-(N-dodecylcarbamoyloxymethyl)-5-triethylsilylfuran (Compound 32, 80 mg, 0.19 mmol), water (ca. 0.1 ml) and Rose Bengal (ca. 3 mg) in tetrahydrofuran (5 ml) was exposed to singlet oxygen at 0° for 1.5 hours. The residue, after solvent removal, was purified by chromatography on preparative silica thin layer plates (developed with ethyl acetate) to give the title furanone as a colorless oil.

$^1$HNMR (CDCl$_3$) 0.92 (t, 3H, J =6.8 Hz), 1.29 (br s, 20H), 1.55 (br m, 2H), 3.20 (dd, 2H, J =6.3 Hz), 4.95 (br, 1H), 5.20 (br, 1H), 6.07 (br s, 1H) and 6.16 (br s, 1H).

$^{13}$CNMR (CDCl$_3$) 13.8, 22.5, 26.5, 26.8, 29.6, 28.6, 28.7, 28.8, 29.0, 29.1, 29.4, 29.6, 30.0, 31.7, 41.2, 59.4, 97.9, 118.6, 115.9, 164.4 and 170.7.

EXAMPLE 4

4-Dodecanoxy-2-triethylsilylfuran (Compound 33)

A solution of 4-hydroxymethyl-2-triethylsilylfuran (160 mg, 0.75 mmol) in tetrahydrofuran (0.5 ml) was added to a suspension of potassium hydride (33 mg, 0.83 mmol) in tetrahydrofuran (1 ml) at room temperature. When all the potassium hydride disappeared 1-iodododecane (0.37 ml, 1.5 mmol) was added. Stirring was continued for 4 days at room temperature. The reaction mixture was quenched with water. Extraction (ethyl ether) and evaporation of the dried (magnesium sulfate) extracts gave an oil, which was purified by flash chromatography on silica using 5% ethyl ether/hexane. Fractions with R$_f$of about 0.65 on evaporation gave the titled ether as a pale yellow oil.

$^1$HNMR (CDCl$_3$) 0.76 (q, 6H J =7.6 Hz), 0.91 (t, 3H, J =6.9 Hz), 1.00 (t, 9H, J=7.3 Hz) 1.29 (br s, 18H), 1.65 (m, 2H), 2H) and 7.63 (s, 3.47 (t, 2H, J =6.7 Hz), 4.39 (s, 2H), 6.68 (s, 1H).

HRMS exact mass calculated for C$_{23}$H$_{44}$O$_2$Si(M+) 380.3111, found 380.3100.

4-(Dodecanoxy)-5-hydroxy-2!5U)-furanone (Compound 7)

A mixture of 4-dodecanoxy-2-triethylsilylfuran (Compound 33, 85 mg, 0.22 mmol), water (0.05 ml) and Rose Bengal (ca. 3 mg) in tetrahydrofuran (6 ml) was exposed to singlet oxygen at 0° for 1.5 hours. The residue, after solvent removal, was purified by chromatography on preparative silica plates (20x20cm, 1000u, developed with 50% ethyl ether/hexane) to give the title furanone as a colorless solid.

$^1$HNMR (CDC13) 0.92 (t, 3H, J =6.9 Hz), 1.30 (br s, 18H), 1.64 (m, 2H), 3.57 (t, 2H, J =6.6 Hz), 4.37 (br s, 2H), 5.75 (br, 1H), 6.10 (s, 1H) and 6.16 (s, 1H).

$^{13}$C NMR (CDCl$_3$) 14.1, 22.6, 25.9, 29.3, 29.4, 29.5, 29.6, 31.9, 65.7, 71.9, 97.9, 117.9, 166.5 and 171.5.

HRMS exact mass calculated for C$_{17}$H$_{31}$O$_4$(M+H)+ 299.2222, found 299.2204.

EXAMPLE 5

(E),(Z)-)-0-Methyl-2-triethylsilyl-4-furaldehyde oxime (Compound 28)

A solution of sodium acetate (1 g, 12.3 mmol) and methoxylamine hydrochloride (1.05 g, 12.3 mmol) in water (5 ml) was added to a solution of 2-triethylsilyl-4-furaldehyde (Compound 23, 860 mg, 4.1 mmol) in ethanol (6 ml) at room temperature. After stirring for 16 hours, most of the ethanol was evaporated and the residue dissolved in water. Extraction (ethyl acetate) and evaporation of the dried (magnesium sulfate) extracts gave an oil, which was purified by flash chromatography on silica using 5% ethyl ether/hexane to give the title oxime as a colorless oil $^1$HNMR (CDC13) 0.79 (q, 6H, J = 7.3 Hz), 0.99 (t, 9H, J = 7.9 Hz), 3.95 (s, 3H), 4.06 (s, 3H), 6.84 (s, 1H), 7.00 (s, 1H), 7.28 (s, 1H), 7.82 (s, 1H), 8.05 (s, 1H) and 8.34 (s, 1H).

HRMS exact mass calculated for $C_{12}H_{21}NO_2Si(M+)$ 239.1341, found 239.1332.

4-AMINOMETHYL-2-TRIETHYLSILYLFURAN (COMPOUND 29)

Lithium aluminum hydride (a 1.0 M solution in tetrahydrofuran; 0.54 ml, 0.54 mmol) was added dropwise to a solution of (E),(Z-O-methyl-2-triethylsilyl-4-furaldehyde oxime (Compound 28, 106.2 mg, 0.46 mmol) in tetrahydrofuran (5 ml) at room temperature. After stirring at room temperature overnight (ca. 14 hours), the reaction mixture was quenched with water. Extraction (ethyl ether) and evaporation of the dried (magnesium sulfate) extracts gave an oil, which was purified by flash chromatography on silica using 10% methanol/dichloromethane/1% ammonia. Fractions with $R_f$ of about 0.34 gave after evaporation the title amine as a pale yellow oil.

$^1$H NMR (CDC13) 0.76 (q, 6H, J = 7.9 Hz), 0.98 (t, 9H, J = 8.4 Hz), 1.87 (br s, 2H), 3.76 (s, 2H), 6.63 (s, 1H) and 7.56 (s, 1H)

HRMS exact mass calculated for $C_{11}H_{21}SiNO(M+)$ 211.1392, found 211.1389.

4-(N-Dodecanoylaminomethyl)-2-triethylsilylfuran (Compound 34)

Dodecanoyl chloride (109 mg, 0.49 mmol) was added to a solution of 4-aminomethyl-2-triethylsilylfuran (Compound 29, 70 mg, 0.33 mmol) and triethylamine (69 microliter, 0.49 mmol) in tetrahydrofuran (3 ml) at room temperature. After stirring at room temperature overnight (ca. 15 hours), most of the solvent was evaporated and the residue was purified by chromatography on preparative silica thin layer plates (developed with 50% ethyl ether/hexane) to give the title amide as a colorless oil.

$^1$HNMR (CDCl$_3$) 0.75 (q, 6H, J = 7.9 Hz), 0.87 (t, 3H, J = 6.8 Hz), 0.97 (q, 9H, J = 7.9 Hz), 1.24 (br s, 16H), 1.60 (m, 2H), 2.17 (t, 2H, J = 7.8 Hz), 4.27 (d, 2H, J = 5.3 Hz), 5.65 (br s, 1H), 6.57 (s, 1H) and 7.56 (s, 1H).

HRMS exact mass calculated for $C_{23}H_{43}NO_2Si(M+)$ 393.3063, found 393.3048.

4-(N-Dodecanoylaminomethyl)-5-hydroxy-2(5H)-furanone (Compound 8)

A mixture of 4-(N-dodecanoylaminomethyl)-2-triethylsilylfuran (Compound 24, 73.2 mg, 0.18 mmol), water (0.05 ml) and Rose Bengal (ca. 3 mg) in tetrahydrofuran (5 ml) was exposed to singlet oxygen at 0° for 1.5 hours. The residue, after solvent removal, was purified by chromatography on preparative silica thin layer plates (developed with ethyl acetate to give the title furanone as an off-white solid.

$^1$HNMR (CDCl$_3$) 0.93 (t, 3H, J = 6.9 Hz), 1.30 (br s, 16H), 1.65 (br m, 2H), 2.31 (t, 2H, J = 7.8 Hz), 4.22 (d, 2H, J = 5.0 Hz), 5.93 (s, 1H), 6.11 (s, 1H) and 7.04 (t, 1H, J = 5.0 Hz).

$^{13}$CNMR (CD$_3$OD) 14.5, 23.7, 26.9, 30.3, 30.5, 30.6, 30.7, 33.0, 36.8, 37.7, 100.0, 118.1, 168.7, 172.6 and 176.4.

HRMS exact mass calculated for $C_{17}H_{30}NO_4(M+H)^+$ 312.2174, found 312.2182.

EXAMPLE 6

4-(N-Dodecylureido)methyl-2-triethylsilylfuran (Compound 35)

Dodecylisocyanate (105 mg, 0.49 mmol) was added to a solution of 4-aminomethyl-2-triethylsilylfuran (compound 29, 70 mg, 0.33 mmol) and triethylamine (69 microliter, 0.49 mmol) in tetrahydrofuran (3 ml) at room temperature. After stirring at room temperature overnight (ca. 16 hours), the reaction mixture was quenched with water. Extraction (ethyl ether) and evaporation of the dried (magnesium sulfate) extracts gave a residue which was purified by flash chromatography on silica using 60% ethyl ether/hexane. Fractions of $R_f$ of about 0.47 on evaporation gave the title urea as an off-white solid.

$^1$HNMR (CDC13) 0.74 (q, 6H, J = 8.0 Hz), 0.87 (t, 3H, J = 6.9 Hz), 0.96 (q, 9H, J = 7.7 Hz), 1.24 (br s, 18H), 1.40 (m, 2H), 3.15 (q, 2H, J = 6 4 Hz), 4.17 (d, 2H), J = 5.4 Hz), 4.67 (br t, 1H), 4.85 (br t, 1H), 6.58 (s, 1H) and 7.53 (s, 1H).

HRMS exact mass calculated for $C_{24}H_{46}N_2O_2Si(M+)$ 422.3329 found 422.3315.

4-(N-Dodecylureido)methyl-5-hydroxy-2(5H)-furanone (Compound 9)

A mixture of 4-(N-dodecylureido)methyl-2-triethylsilylfuran (Compound 35, 80 mg, 0.19 mmol), water (0.01 ml) and Rose Bengal (ca. 3 mg) in tetrahydrofuran (6 ml) was exposed to singlet oxygen at 0° for 1 hour. The residue, after solvent removal, was purified by chromatography on preparative silica thin layer plates (developed with ethyl acetate) to give the title furanone as a colorless solid.

$^1$HNMR (CD$_3$OD) 0.93 (t, 3H, J = 7.2 Hz), 1.33 (br s, 18H), 1.50 (br t, 2H), 3.16 (t, 2H, J = 6.9 Hz), 4.12 (br s, 2H), 4.91 (s, 2H), 5.91 (br s, 1H) and 6.09 (s, 1H).

$^{13}$CNMR (CD$_3$OD) 14.5, 23.7, 27.9, 30.5, 30.8, 31.0, 31.3, 33.1, 38.6, 41.1, 99.9, 117.6, 160.7, 170.7 and 172.8.

HRMS exact mass calculated for $C_{18}H_{33}N_2O_4(M+H)^+$ 341.2440, found 341.2434.

EXAMPLE 7

4-(N-Dodecylsulfonamido)methyl-2-triethylsilylfuran (Compound 36)

Dodecanesulfonyl chloride (124 mg, 0.46 mmol) was added to a solution of 4-aminomethyl-2-triethylsilylfuran (Compound 29, 81.3, mg, 0.39 mmol) and triethylamine (64 microliter, 0.46 mmol) in tetrahydrofuran (2 ml) was also added. After stirring at room temperature overnight (ca. 18 hours), the reaction mixture was quenched with water. Extraction (ethyl ether) and evaporation of the dried (magnesium sulfate) extracts gave an oil, which was purified by chromatography on preparative silica thin layer plates (developed with 30% ethyl ether/hexane) to give the title sulfonamide as a pale yellow oil.

$^1$HNMR (CDCl$_3$) 0.74 (q, 6H, J = 7.9 Hz), 0.88 (t, 3H, J = 7.8 Hz), 0.95 (t, 9H, J = 7.4 Hz), 1.26 (br s, 18H), 1.75 (m, 2H), 2.94 (m, 2H), 4.17 (d, 2H, J = 5.9 Hz), 4.35 (t, 1H, J = 5.9 Hz) 6.64 (s, 1H) and 7.63 (s, 1H).

FABMS 444(M+H)$^+$

4-(N-Dodecylsulfonamido)-methyl-5-hydroxy-2(5H)-furanone (Compound 10)

A mixture of 4-(N-dodecylsulfonamido)methyl-2-triethylsilylfuran (Compound 36, 106 mg, 0.24 mmol), water (0.01 ml) and Rose Bengal (ca. 3 mg) in tetrahydrofuran (6 ml) was exposed to singlet oxygen at 0° for 1.5 hours. The residue, after solvent removal, was purified by chromatography on preparative silica thin layer plates (developed with 50% ethyl acetate/hexane) to give the title furanone as a colorless solid.

$^1$HNMR (CD$_3$OD) 0.95 (t, 3H, J =6.8 Hz), 1.34 (br s, 16H), 1.50 (m, 2H), 1.80 (m, 2H), 3.15 (m, 2H), 4.11 (br s, 2H), 4.92 (br s, 2H), 6.15 (s, 1H) and 6.17 (s, 1H).

$^{13}$CNMR (CD$_3$OD) 14.3, 23.6, 24.6, 29.2, 30.2, 30.4, 30.6, 30.7, 40.9, 53.5, 100.2, 119.3, 168.9 and 172.9.

FABMS 362[(M+H)+,18]

EXAMPLE 8

Bis-[(2-triethylsilyl-4-furyl)methyl]oxalate (Compound 27)

Oxalyl chloride (0.59 ml, 6.79 mmol) was added dropwise to a solution of 4-hydroxymethyl-2-triethylsilylfuran (compound 24, 1.2 g, 5.66 mmol) and triethylamine (0.95 ml, 6.79 mmol) in dichloromethane (10 ml) at 0o After 10 minutes, the reaction mixture was quenched with ice. Extraction (dichloromethane) and evaporation of the dried (magnesium sulfate) extracts gave an oil, which was purified by flash chromatography on silica using 5% ethyl ether/hexane. Fractions with R$_f$ of about 0.17 gave, after evaporation the title oxalate ester as a colorless oil.

$^1$HNMR (CDC1$_3$) 0.81 (q, 6H, J =7.3 Hz), 1.02 (t, 9H, J - 7.3 Hz), 5.24 (s, 2H), 6.73 (s, 1H) and 7.78 (s, 1H).

MS m/e (% abundance) 195(100), 167(16), 115(35) and 87(29).

4-Iodomethyl-2-triethylsilylfuran (compound 26)

A mixture of bis-[(2-triethylsilyl-4-furyl)methyl]oxalate (Compound 27, 823 mg, 1.72 mmol) and sodium iodide (5.36 g, 35.8 mmol) in acetone (7 ml) was stirred at room temperature for 1 day and quenched with water. Extraction (pentane) and evaporation of the dried (magnesium sulfate) extracts gave the titled iodide, which was used in the next step without further purification.

4-Dodecanthiolmethyl-2-triethylsilylfuran (Compound 37)

Dodecanthiol (0.52 ml, 2.19 mmol) was added dropwise to a suspension of potassium hydride (88 mg, 2.19 mmol) in tetrahydrofuran (10 ml) at room temperature under argon. After 3 hours hexamethylphosphoramide (2 ml), followed by a solution of 4-iodomethyl-2-triethylsilylfuran (Compound 26, 470 mg, 1.45 mmol) in tetrahydrofuran (2 ml) was added. Stirring was continued for 8 days at room temperature and the reaction mixture was quenched with water. Extraction (ethyl ether) and evaporation of the dried (magnesium sulfate) extracts gave a residue, which was purified by flash chromotography on silica using 5% ethyl ether/hexane. Fractions with Rf of about 0.18 gave after evaporation the title thioether as a colorless oil.

$^1$HNMR (CDCl$_3$) 0.76 (q, 6H, J =7.7 Hz), 0.79 (t, 3H, J =6.7 Hz), 0.98 (t, 9H, J =7.3 Hz), 1.28 (br s, 18H), 1.55 (m, 2H), 2.47 (t, 2H, J =7.6 Hz), 3.58 (s, 2H), 6.66 (s, 1H) and 7.56 (s, 1H).

HRMS exact mass calculated for C$_{23}$H$_{44}$SSiO(M+) 396.2882, found 396.2885.

4-Dodeoanethiomethvl-5-hydroxy-2(5H)-furanone (Compound 11)

A mixture of 4-dodecanthiomethyl-2-triethylsilylfuran (Compound 37, 180 mg, 0.46 mmol), water (0.01 ml) and Rose Bengal (ca. 3 mg) in tetrahydrofuran (6 ml) was exposed to singlet oxygen at 0° for 1 hour. The residue, after solvent removal, was purified by chromatography on preparative silica thin layer plates (developed with 60% ethyl ether/hexane) to give the title furanone as a pale yellow oil.

$^1$HNMR (CDC13) 0.91 (t, 3H, J =6.9 Hz), 1.29 (br s, 18H), 1.61 (m, 2H), 2.52 (t, 2H, J =7.2 Hz), 3.50 (br, 2H), 5.85 (br, 1H), 6.00 (s, 1H) and 6.28 (s, 1H).

$^{13}$CNMR (CDCl$_3$) 14.1, 22.6, 27.6, 28.7, 28.9, 29.2, 29.3, 29.5, 29.6, 31.9, 32.1, 98.3, 118.8, 165.7 and 171.5.

HRMS exact mass calculated for C$_{17}$H$_{30}$SO$_3$(M+) 314.1915, found 314.1911.

EXAMPLE 9

4-(Dodecanesulfoxomethyl)-5-hydroxy-2(5H)-furanone (Compound 12)

A mixture of 4-dodecanethiomethyl-5-hydroxy-2-(5H)-furanone (Compound 11, 36.1 mg, 0.12 mmol) and 30% hydrogen peroxide (1 ml) in methanol (1.5 ml) was stirred at room temperature for 18 hours. Most of the solvent was removed and the residue was purified by chromatography on preparative silica thin layer plates (developed with ethyl acetate) to give the title furanone.

$^1$HNMR (CDCl$_3$) 0.89 (t, 3H), 1.25 (br s, 18H), 1.75 (m, 2H), 2.85 (m, 2H), 3.75 (m, 1H), 4.00 (m, 1H) and 6.20 (m, 2H).

HRMS exact mass calculated for C$_{17}$H$_{31}$O$_4$S (M+H)+ 331.1943, found 331.1947.

EXAMPLE 10

Diethyl (2-triethylsilyl-4-furyl)methyl phosphate (Compound 38)

A mixture of (2-triethylsilyl-4-furyl)methanol (Compound 24, also known as 4-hydroxymethyl-2-triethylsilylfuran 2.86 g, 13.5 mmol), triethylamine (3.76 ml, 27.0 mmol) and diethyl chlorophosphate (4.28 ml, 29.0 mmol) in tetrahydrofuran (10 ml) was stirred at room temperature for 14 hours. The mixture was filtered and the filtrate was evaporated to dryness to give a residue, which was redissolved in ethyl ether and washed with 10% hydrochloric acid, water and 5% sodium bicarbonate. Evaporation of the dried (magnesium sulfate) organic phase gave an oil, which was purified by chromatography on a silica column with 30% ethyl acetate/hexane to give the title ester.

IR(CDCl$_3$): 1260 and 1220.

$^1$HNMR ( CDCL$_3$): 0.70 (q, 6H, J=7.8Hz), 0.92 (t, 9H, J=7.8 Hz), 1.24 (t, 6H, J =7.1 Hz), 4.01 (q, 2H, J =6.8 Hz), 4.03 (q, 2H, J - 6.8 Hz), 4.90 (s, 1H), 4.93 (s, 1H), 6.66 (s, 1H) an 7.64 (s, 1H).

$^{13}$CNMR (CDCl$_3$) 3.0 , 7.1, 15.8, 15.9, 60.6, 60.7, 63.5, 63.6, 120.5, 120.6, 121.0, 145.5 AND 159.7.

4-1-Diethylohosohoyloxy)Methyl-5-hydroxy-2(5H)-furanone (Compound 13)

A mixture of diethyl (2-triethylsilyl-4-furyl)methyl phosphate (Compound 38, 803 mg, 2.31 mmol), water (2 drops) and Rose Bengal (5 mg) in acetone (50 ml) was exposed to singlet oxygen at 0° for 7 hours. The residue, after solvent removal, was purified by chromatography on a silica column using ethyl acetate to give the title furanone.

IR (CHCl$_3$) 3250, 1770, 1250, 1150, 1050 and 960.

$^1$HNMR (CDCl$_3$): 1.37 (t, 6H, J =6.0 Hz), 4.16 (2q, 4H, J =6.0 Hz), 4.85 (ddd, 1H, J =15.0 Hz, 9.0 Hz, 1.2 Hz); 4.96 (ddd, 1H, J =15.0 Hz, 7.2 Hz; 0.6 Hz), 6.12 (s, 1H) and 6.15 (s, 1H).

$^{13}$CNMR (CDCl$_3$) 62.1, 64.7, 97.4, 118.8, 163.3, 163.4 and 170.4.

EXAMPLE 11

4-1-(Diethylohosohoryloxy)methyl-5-dodecyloxy-2(5H)-furanone (Compound 14)

A mixture of 4-(1-diethylphosphoryloxy)methyl-5-hydroxy-2(5H)-furanone (Compound 13, 282 mg, 1.06 mmol), pyridine (0.11 ml, 1.44 mmol) and dodecanoylchloride (0.56 ml, 2.4 mmol) in tetrahydrofuran (5 ml) was stirred at room temperature for 14 hours. The mixture was quenched with water and washed with dilute hydrochloric acid, copper sulfate and water. Evaporation of the dried (magnesium sulfate) extracts gave an oil which was purified by a silica column using 60% ethyl acetate/hexane to give the title ester.

IR (CHCl$_3$) 1800, 1770 and 1030.

$^1$HNMR (CDCl$_3$): 0.72 (t, 3H, J =7.0 Hz), 1.10 (br s, 16H), 1.20 (t, 6H, J =6.8 Hz), 1.50 (m, 2H), 2.26 (t, 2H, J =7.6 Hz) 4.00 (p, 4H, J =7.1 Hz), 4.72 (m, 2H), 6.11 (br s, 1H) and 6.81 (br s, 1H).

$^{13}$CNMR (CDCl$_3$): 13.5, 15.5, 15.6, 22.2, 23.9, 28.5, 28.7, 28.8, 28.9, 29.1, 31.4, 33.3, 61.0, 61.1, 64.1, 64.2, 92.0, 119.6, 161.2, 161.3, 168.7 and 171.6.

EXAMPLE 12

4-Hydroxymethyl-2-triethylsilylfuran (Compound 24) is reacted with 2-chloro-2-oxo-1,3,2-dioxaphospholane and 4-dimethylaminopyridine and the resulting 2-(2-triethylsilyl-4-furyl)methoxy-2-oxo-1,3,2-dioxaphospholane is reacted with trimethylamine in acetonitrile to give (2-triethylsilyl-4-furyl)phosphocholine. Treatment of this intermediate with singlet oxygen and using Rose Bengal as initiator gives 4-phosphochloline)-methyl-5-hydroxy-2(5H)-furanone (Compound 15).

EXAMPLE 13

1-Dodecanol is reacted with triphosgene and 4-aminomethyl-2-triethylsilylfuran (Compound 29) to give (4-N-(dodecyloxycarbonyl)methylamino-2-triethylsilyl-furan. Treatment of this intermediate with singlet oxygen and using Rose Bengal as initiator gives 4-N-(dodecyloxycarbonyl)methylamino-5-hydroxy-2(5H)-furanone (Compound 16).

EXAMPLE 14

4-Aminomethyl-2-triethylsilylfuran (Compound 29) is reacted with dodecylphosphinic dichloride and potassium hydroxide to give dodecyl N-(2-triethylsilyl-4-furyl)methyl phosphoramide. Treatment of this intermediate with singlet oxygen and using Rose Bengal as initiator gives 4-(dodecylphosphoramidomethyl)-5-hydroxy-2-(5H)-furanone (Compound 17).

EAXMPLE 15

Oxidizing 4-dodecylthiomethyl-2-triethylsilylfuran with potassium peroxymonosulfate gives 4-dodecylsulfonylmethyl-2-triethylsilylfuran. Treatment of this intermediate with singlet oxygen and using Rose Bengal as initiator gives 4-(dodecylsulfonylmethyl)5-hydroxy-2(5H)-furanone (Compound 18).

EXAMPLE 16

Treatment of 4-methoxybenzaldehyde with (4-carboxybutyl)triphenylphosphonium bromide and potassium bis(trimethylsilyl)-amide yields 6-(4-methoxyphenyl)-5-hexen-1-oic acid which is hydrogenated over palladium on carbon. The resulting 6-(4-methoxyphenyl)-hexan-1-oic acid is coupled to 4-hydroxymethyl-2-triethylsilylfuran (Compound 24) using dicyclohexylcarbodiimide and 4-dimethylaminopyridine to give (2-triethylsilyl-4-furyl)methyl (4-methoxyphenyl)hexanoate. This intermediate is reacted with singlet oxygen, using Rose Bengal as initiator, to give 4-[4-methoxyphenyl)hexanoyloxymethyl]-5-hydroxy-2(5H)-furanone (Compound 19).

EXAMPLE 17

Reacting 1-dodecylamine with sulfuryl chloride and 4-(aminomethyl)-2-triethylsilylfuran (compound 29) gives N-dodecyl-N'-(2-triethylsilyl-4-furyl)methyl sulfonylurea. Oxidation of the resulting sulfonyl urea with oxygen, using Rose Bengal as initiator, gives 4-[(dodecylaminosulfonyl)aminomethyl]-5-hydroxy-2(5H)furanone (Compound 20).

EXAMPLE 18

Diethyl (2-triethylsilyl-4-furyl)methyl phosphate (Compound 38) is reacted with trimethylsilyl bromide to give (2-triethylsilyl-4-furyl)methyl phosphate. Oxidation using oxygen and using Rose Bengal as initiator gives 4-phosphoryloxymethyl-5-hydroxy-2(5H)-furanone. Esterification of this furanone with dodecanoyl chloride gives 4-phosphoryloxymethyl-5-dodecyloxy-2(5H)-furanone (Compound 21).

What is claimed is:

1. A compound of the formula

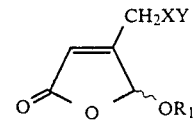

wherein
R$_1$ is H or alkyl of 1 to 20 carbons, CO-R$_1$* CO—O—R$_1$* CO-NH-R$_1$* or PO( OR$_1$*)$_2$ or PO-(OR$_1$*)R$_1$* where R$_1$* independently is alkyl of 1 to 20 carbons, or phenyl with the proviso that when R$_1$ is CO—NH—R$_1$* then R$_1$* is not H;

X is O, S, SO-, SO$_2$, NH-, or NR$_2$ where R$_2$ is phenyl, or alkyl of 1 to 20 carbons, and Y is alkyl 6 to 25 carbon atoms, aryl C$_1$-C$_6$-alkyl, aryl, alkenyl containing one or more olephinic bonds and 6 to 25 carbon atoms, CO—R$_3$, CO—OR$_3$, CONHR$_3$, SO$_2$R$_3$, SO$_2$NHR$_3$ where R$_3$ is aryl, alkyl of 4 to 25 carbons, alkenyl of 4 to 25 carbons containing one or more olephinic bonds, further Y is (CH$_2$)$_n$—O—R$_4$, or (CH$_2$)$_n$—O—(CH$_2$)$_m$—O— R$_4$, where n, and m, are integers and are independently 1 to 25 and R$_4$ is phenyl or alkyl of one to 20 carbons, still further Y is PO(OH)$_2$, PO(OH)OR$_5$, PO(OH)R$_5$ PO(OR$_5$)$_2$, where R$_5$ is independently phenyl, alkyl of 1 to 20 carbons or R$_5$ is (CH$_2$)$_n$—N(R$_5$*)$_3$ where R$_5$* is alkyl of 1 to 20 carbons, or Y is NH—R$_6$ where R$_6$ is phenyl, or alkyl of 6 to 25 carbon atoms with the proviso that when X is O, S, then Y is not NH—R$_6$, and with the further proviso that when X is SO or SO$_2$ then Y is not SO$_2$R$_3$ or SO$_2$NHR$_3$, or a pharmaceutically acceptable salt thereof.

2. A compound of claim 1 wherein R$_1$ is H, CH$_3$CO or COR$_1$* where R$_1$* is long chain alkyl containing 4 to 25 carbons.

3. A compound of claim 2 where R$_1$* is n-dodecyl.

4. A compound of claim 1 where X is O.

5. A compound of claim 1 where X is S.

6. A compound of claim 1 where X is NH.

7. A compound of claim 1 where X is SO.

8. A compound of claim 1 where X is SO$_2$.

9. A compound of claim 1 where Y is long chain alkyl having 10 to 25 carbons.

10. A compound of claim 1 where Y is (CH$_2$)$_n$—O—(CH$_2$)$_m$—O—R$_4$.

11. A compound of claim 1 where Y is selected from a group consisting of COR$_3$, COOR$_3$ and CONHR$_3$ where R$_3$ is long chain alkyl having 6 to 25 carbons.

12. A compound of claim 1 where Y is phenyl C$_4$-C$_{25}$ alkyl.

13. A compound of claim 1 where Y is selected from a group consisting of SO$_2$R$_3$, and SO$_2$NHR$_3$, where R$_3$ is long chain alkyl having 4 to 25 carbons.

14. A compound of claim 1 where Y is selected from a group consisting of PO(OH)$_2$, PO(OH)R$_5$, PO(OR$_5$)$_2$ and PO(OH)O(CH$_2$)$_n$—N$^+$(R$_5$*)$_3$.

15. A compound of the formula

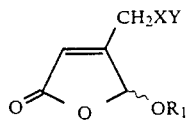

wherein
R$_1$ is H, CO—R$_1$*, CO—O—R$_1$*, CO—NH—R$_1$* or PO(OR$_1$I)$_2$ or PO(OR$_1$*)R$_1$* where R$_1$* is H, or alkyl of 1 to 20 carbons;
X is O, S, SO—, SO$_2$, NH—, and
Y is alkyl having 6 to 25 carbon atoms, aryl-C$_1$-C$_6$alkyl, CO—R$_3$, CO—OR$_3$, CONHR$_3$, SO$_2$R$_3$, SO$_2$NHR$_3$, (CH$_2$)$_n$—O—R$_4$, (CH$_2$)$_n$—O—(CH$_2$)$_m$—O—R$_4$, PO(OH)$_2$, PO(OH)R$_5$ PO(OR$_5$)$_2$, PO(OH)OR$_5$ and NH-R$_6$, where R$_3$ is aryl-C$_1$-C$_6$alkyl, alkyl having 6 to 25 carbons, n, and m, are integers and are independently 1 to 25, R$_4$ is alkyl of one to 20 carbons, R$_5$ is independently alkyl of 1 to 20 carbons or R$_5$ is O(CH$_2$)$_2$—N(R$_5$*)$_3$ where R$_5$ * is lower alkyl of 1 to 6 carbons, R$_6$ is phenyl, or alkyl of 6 to 25 carbon atoms with the proviso that when X is O, S, then Y is not NH—R$_6$, and with the further proviso that when X is SO or SO$_2$ then Y is not SO$_2$R$_3$ or SO$_2$NHR$_3$, or a pharmaceutically acceptable salt thereof.

16. A compound of claim 15 wherein X is O.

17. A compound of claim 16 wherein Y is (CH$_2$)$_n$—O—(CH$_2$)$_m$—O—R$_4$.

18. A compound of claim 17 wherein Y is (CH$_2$)—O—(CH$_2$)$_2$—O—CH$_3$.

19. The compound of claim 18 wherein R$_1$ is hydrogen.

20. A compound of claim 16 wherein Y is PO(OH)R$_5$ where R$_5$ is long chain alkyl of 4 to 25 carbon atoms, or Y is PO(OH)O(CH$_2$)$_2$—N(r$_5$*)$_3$ where R$_5$ * is lower alkyl of 1 to 6 carbon atoms.

21. A compound of claim 20 wherein Y is PO(OH)(CH$_2$)$_{11}$CH$_3$.

22. The compound of claim 21 wherein R$_1$ is hydrogen.

23. A compound of claim 20 wherein Y is PO(OH)O(CH$_2$)$_2$—N(R$_5$*)$_3$ and R$_5$* is CH$_3$.

24. The compound of claim 23 where R$_1$ is H.

25. A compound of claim 16 wherein Y is PO(OH)$_2$ or PO(OR$_5$)$_2$ where R$_5$ is lower alkyl of 1 to 6 carbon atoms.

26. A compound of claim 25 wherein Y is PO(OH)$_2$.

27. The compound of claim 26 where R$_1$ is H.

28. The compound of claim 26 where R$_1$ is CO(CH$_2$)$_{10}$CH$_3$.

29. A compound of claim 25 wherein R$_5$ is ethyl.

30. The compound of claim 29 where R$_1$ is H.

31. The compound of claim 29 where R$_1$ is CO(CH$_2$)$_{10}$CH$_3$.

32. A compound of claim 16 wherein Y is CO—R$_3$ and R$_3$ is aryl-C$_1$-C$_6$alkyl.

33. A compound of claim 32 wherein R$_3$ is (CH$_2$)$_5$—(4-methoxy)phenyl.

34. A compound of claim 33 where R$_1$ is H.

35. A compound of claim 16 wherein Y is CONHR$_3$.

36. A compound of claim 35 wherein R$_3$ is (CH$_2$)$_{11}$CH$_3$.

37. The compound of claim 36 where R$_1$ is H.

38. A compound of claim 16 wherein Y is alkyl having 6 to 25 carbon atoms.

39. A compound of claim 38 wherein Y is (CH$_2$)$_{11}$CH$_3$.

40. The compound of claim 39 where R$_1$ is H.

41. A compound of claim 15 wherein X is NH.

42. A compound of claim 41 wherein Y is CO—R$_3$, CO—OR$_3$, CO—NHR$_3$.

43. A compound of claim 42 wherein Y is CO—R$_3$ and R$_3$ is (CH$_2$)$_{11}$CH$_3$.

44. The compound of claim 43 wherein R$_1$ is H.

45. A compound of claim 42 wherein Y is CO—NHR$_3$ and R$_3$ is (CH$_2$)$_{11}$CH$_3$.

46. The compound of claim 45 wherein R$_1$ is H.

47. A compound of claim 42 wherein Y is CO—OR$_3$ and R$_3$ is (CH$_2$)$_{11}$CH$_3$.

48. The compound of claim 47 wherein R$_1$ is H.

49. A compound of claim 41 Wherein Y is SO$_2$R$_3$, SO$_2$NHR$_3$ or PO(OH)R$_5$.

50. A compound of claim 49 wherein Y is SO$_2$R$_3$ and R$_3$ is (CH$_2$)$_{11}$CH$_3$.

51. The compound of claim 50 wherein R$_1$ is H.

52. A compound of claim 49 wherein Y is SO$_2$NHR$_3$ and R$_3$ is (CH$_2$)$_{11}$CH$_3$.

53. The compound of claim 52 wherein R$_1$ is H.

54. A compound of claim 49 wherein Y is PO(OH)R$_5$ and R$_5$ is (CH$_2$)$_{11}$CH$_3$.

55. The compound of claim 54 wherein R$_1$ is H.

56. A compound of claim 15 wherein X is S, SO—, or SO$_2$.

57. A compound of claim 56 wherein X is S and Y is (CH$_2$)$_{11}$CH$_3$.

58. The compound of claim 57 wherein R$_1$ is H.

59. A compound of claim 56 wherein X is SO and Y is (CH$_2$)$_{11}$CH$_3$.

60. The compound of claim 59 wherein R$_1$ is H.

61. A compound of claim 56 wherein X is $SO_2$ and Y is $(CH_2)_{11}CH_3$.

62. The compound of claim 61 wherein $R_1$ is H.

63. An anti-inflammatory pharmaceutical composition including a pharmaceutically acceptable excipient and an amount effective for alleviating symptoms of inflammatory diseases of a compound set forth in the formula

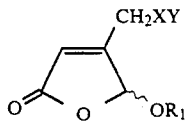

wherein $R_1$ is H or alkyl of 1 to 20 carbons, $CO-R_1^*$ $CO-O-R_1^*$ $CO-NH-R_1^*$ or $PO(OR_1^*)_2$ or $PO(OR_1^*)R_1^*$ where $R_1^*$ independently is alkyl of 1 to 20 carbons, or phenyl with the proviso that when $R_1$ is $CO-NH-R_1^*$ then $R_1^*$ is not H;

X is O, S, SO—, $SO_2$, NH—, or $NR_2$ where $R_2$ is phenyl, or alkyl of 1 to 20 carbons, and Y is alkyl 6 to 25 carbon atoms, aryl $C_1$-$C_6$-alkyl, aryl, alkenyl containing one or more olephinic bonds and 6 to 25 carbon atoms, $CO-R_3$, $CO-OR_3$, $CONHR_3$, $SO_2R_3$, $SO_2NHR_3$ where $R_3$ is aryl, alkyl of 4 to 25 carbons, alkenyl of 4 to 25 carbons containing one or more olephinic bonds, further Y is $(CH_2)_n-O-R_4$, or $(CH_2)_n-O-(CH_2)_m-O-R_4$, where n, and m, are integers and are independently 1 to 25 and $R_4$ is phenyl or alkyl of one to 20 carbons, still further Y is $PO(OH)_2$, $PO(OH)OR_5$, $PO(OH)R_5$ $PO(OR_5)_2$, where $R_5$ is independently phenyl, alkyl of 1 to 20 carbons or $R_5$ is $(CH_2)_n-N(R_5^*)_3$ where $R_5^*$ is alkyl of 1 to 20 carbons, or Y is $NH-R_6$ where $R_6$ is phenyl, or alkyl of 6 to 25 carbon atoms with the proviso that when X is O, S, then Y is not $NH-R_6$, and with the further proviso that when X is SO or $SO_2$ then Y is not $SO_2R_3$ or $SO_2NHR_3$, or a pharmaceutically acceptable salt thereof.

* * * * *

UNITED STATES PATENT AND TRADEMARK OFFICE
CERTIFICATE OF CORRECTION

PATENT NO. : 5,037,811  Page 1 of 3
DATED     : August 6, 1991
INVENTOR(S) : Gary C. M. Lee It is certified that error appears in the above-identified patent and that said Letters Patent is hereby corrected as shown below:

In the Abstract, 18th line of type after the formula, "or" should be --of--;

Column 2, line 65, "$(CH_2)_n-N(R_t^{A*})3$" should be --$(CH_2)_n-N(R_5^*)3$--;

Column 4, line 15, "reagent" should be --reagent--;

Column 7, line 17, "$(R_t^*)3$" should be --$(R_5^*)_3$--;

Column 7, line 38, "1n" should be --in--;

Column 8, line 59, "composition" should be --compositions--;

Column 10, line 40, "Phosoholioase" should be --Pholpholipase--;

Column 12, line 49, "z3" should be --23--;

Column 14, line 4, "furyl-methyl" should be --furyl)methyl--;

Column 14, line 24, after "methanol" delete the --]--;

Column 16, line 51, "2s)." should be --28).--;

Column 16, line 52, "2s)" should be --28)--;

Column 19, line 45, "(CDC13):" should be --$(CDCl_3)$:--;

Column 19, line 47, "(CDC13)" should be --$(CDCl_3)$--;

Column 19, line 67, "(CDC13)" should be --$(CDCl_3)$--;

Column 20, line 51, "4-Hvdroxymethyl"... should be --4-Hydroxymethyl--...;

Column 21, line 2, "(Compound 3)" should be --(Compound 31)--;

Column 21, line 25, "(Dodecylohosohonyloxymethyl)" should be --(Dodecylphosphonyloxymethyl)--;

Column 21, line 39, "(CDC13)" should be --$(CDCl_3)$--;

Column 21, line 64, "(H," should be --9H,--;

UNITED STATES PATENT AND TRADEMARK OFFICE
CERTIFICATE OF CORRECTION

PATENT NO. : 5,037,811
DATED : august 6, 1991
INVENTOR(S) : Gary C.M. lee

It is certified that error appears in the above-indentified patent and that said Letters Patent is hereby corrected as shown below:

Column 22, lines 39-40, "2H) and 7.63 (s, 3.47 (t, 2H, J = 6.7 Hz), 4.39 (s, 2H), 6.68 (s, 1H)." should be --3.47 (t, 2H, J = 6.7 Hz), 4.39 (s, 2H), 6.68 (s, 2H) and 7.63 (s, 1H).--;

Column 22, line 43, ..."2!5U)"... should be ...--2(5H)--...;

Column 22, line 54, "(CDC13)" should be --(CDCl$_3$)--;

Column 23, line 19, "(E),(Z-O-methyl"... should be --(E),(Z)-O-methyl--...;

Column 23, line 30, "(CDC13)" should be --(CDCl$_3$)--;

Column 23, line 63, after "acetate" insert --)--;

Column 24, line 22, "(CDC13)" should be --(CDCl$_3$)--;

Column 25, line 26, "0o" should be --0°--;

Column 25, line 34, "(CDC13)" should be --(CDCl$_3$)--;

UNITED STATES PATENT AND TRADEMARK OFFICE
CERTIFICATE OF CORRECTION

PATENT NO. : 5,037,811
DATED : August 6, 1991
INVENTOR(S) : Gary C.M. Lee

It is certified that error appears in the above-indentified patent and that said Letters Patent is hereby corrected as shown below:

Column 26, line 14, "(CDC13)" should be --($CDCl_3$)--;

Column 26, line 64, "4-1-Diethylohosohoyloxy)Methyl"... should be ---4-1-(Diethylphosphoryloxy)methyl--...;

Column 27, line 14, "4-1-(Diethylohosohoryloxy)"... should be ---4-1-(Diethylphosphoryloxy)--...;

Column 27, line 64, "Eaxmple" should be --Example--; and

Column 29, line 41, Claim 15, "PO($OR_1I)_2$)" should be .

Signed and Sealed this

Twenty-eighth Day of December, 1993

Attest:

BRUCE LEHMAN

Attesting Officer     Commissioner of Patents and Trademarks